United States Patent
Zhang et al.

(10) Patent No.: US 9,790,255 B2
(45) Date of Patent: Oct. 17, 2017

(54) TRANSACTIVATOR OF TRANSCRIPTION (TAT) PROTEINS AND PREPARATION METHOD

(71) Applicant: Sun Yat-Sen University, Guangzhou (CN)

(72) Inventors: Hui Zhang, Guangzhou (CN); Guannan Geng, Guangzhou (CN)

(73) Assignee: Sun Yat-Sen University (CN)

( * ) Notice: Subject to any disclaimer, the term of this patent is extended or adjusted under 35 U.S.C. 154(b) by 0 days.

(21) Appl. No.: 15/113,013

(22) PCT Filed: Jun. 11, 2014

(86) PCT No.: PCT/CN2014/079675
§ 371 (c)(1),
(2) Date: Jul. 20, 2016

(87) PCT Pub. No.: WO2015/188334
PCT Pub. Date: Dec. 17, 2015

(65) Prior Publication Data
US 2017/0044215 A1 Feb. 16, 2017

(51) Int. Cl.
*C07K 14/005* (2006.01)
*A61K 38/00* (2006.01)

(52) U.S. Cl.
CPC ............ *C07K 14/005* (2013.01); *A61K 38/00* (2013.01); *C12N 2740/16322* (2013.01)

(58) Field of Classification Search
CPC ...... C07K 14/005; C07K 14/16; A61K 38/16; A61K 38/00; C12N 2740/16322
See application file for complete search history.

(56) References Cited

FOREIGN PATENT DOCUMENTS

| CN | 102206255 A | 10/2011 |
|---|---|---|
| CN | 103073625 A | 5/2013 |

OTHER PUBLICATIONS

International Search Report for International Patent Application No. PCT/CN2014/079615 dated Dec. 12, 2014.

*Primary Examiner* — Robert Landsman
(74) *Attorney, Agent, or Firm* — Lerner, David, Littenberg, Krumholz & Mentlik, LLP

(57) ABSTRACT

Disclosed is a Tat protein, the amino acid sequence of which is shown as SEQ NO: 1, SEQ NO: 2, SEQ NO: 3 and SEQ NO: 4. The Tat protein of the present invention has been studied and developed and can be a Latent infection of HIV-1 activating potential drug.

3 Claims, 6 Drawing Sheets

Figures 1, 2:
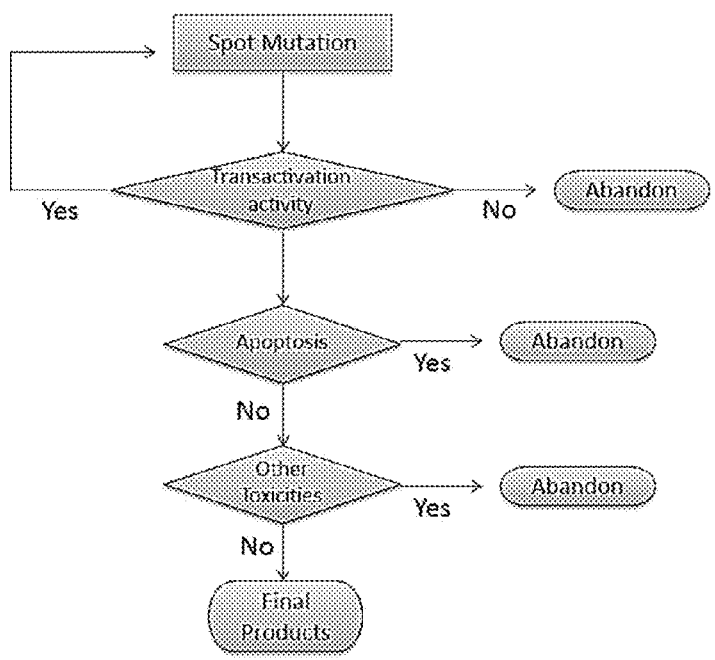
Figure 3:
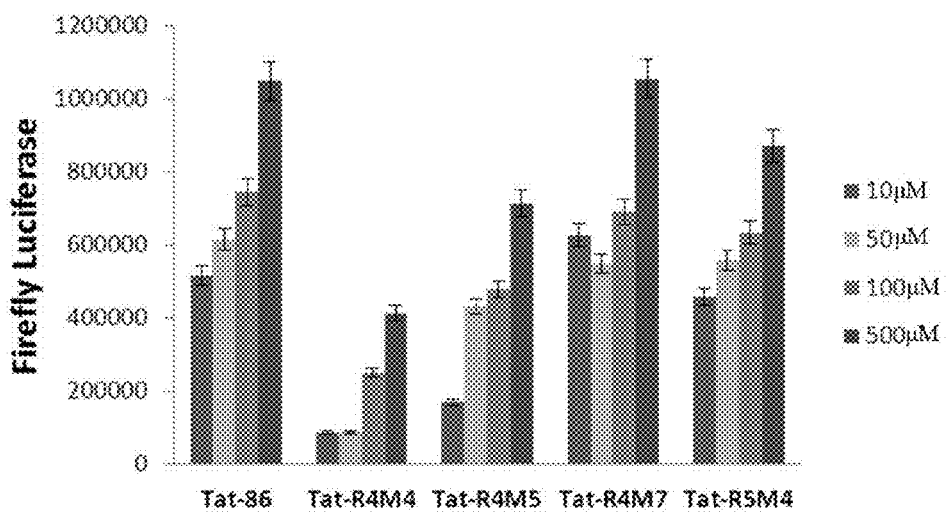
Figure 4:
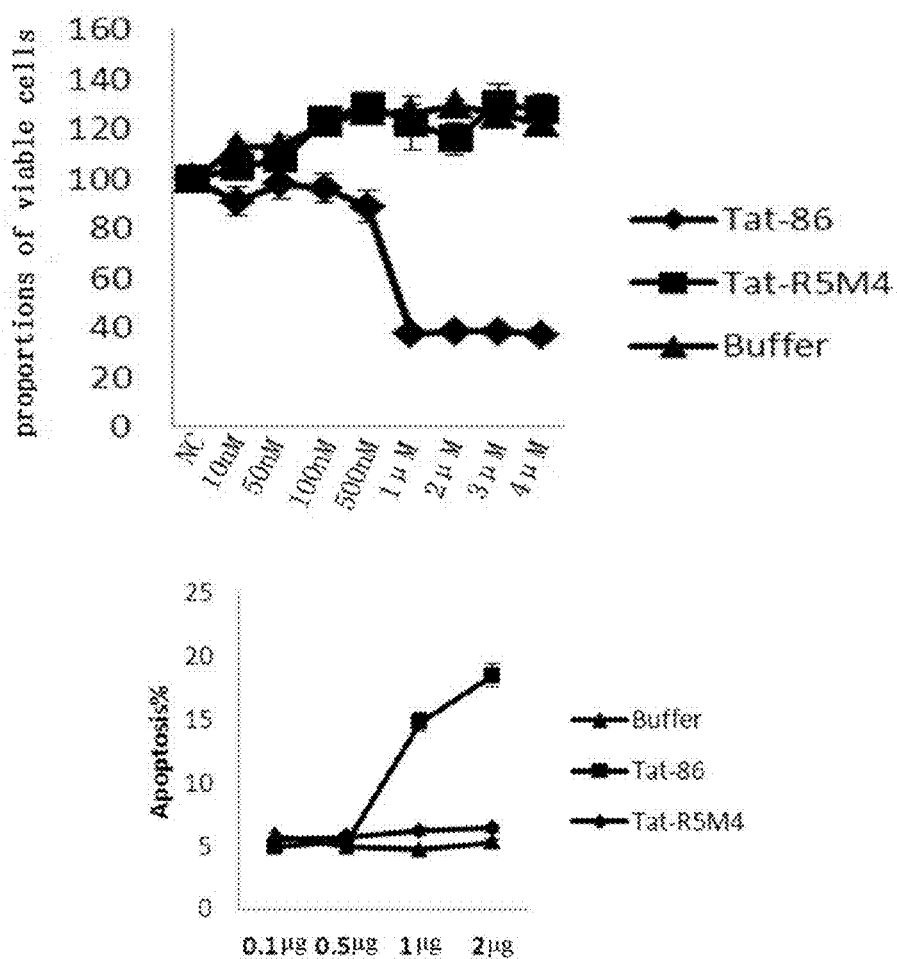
Figure 5:
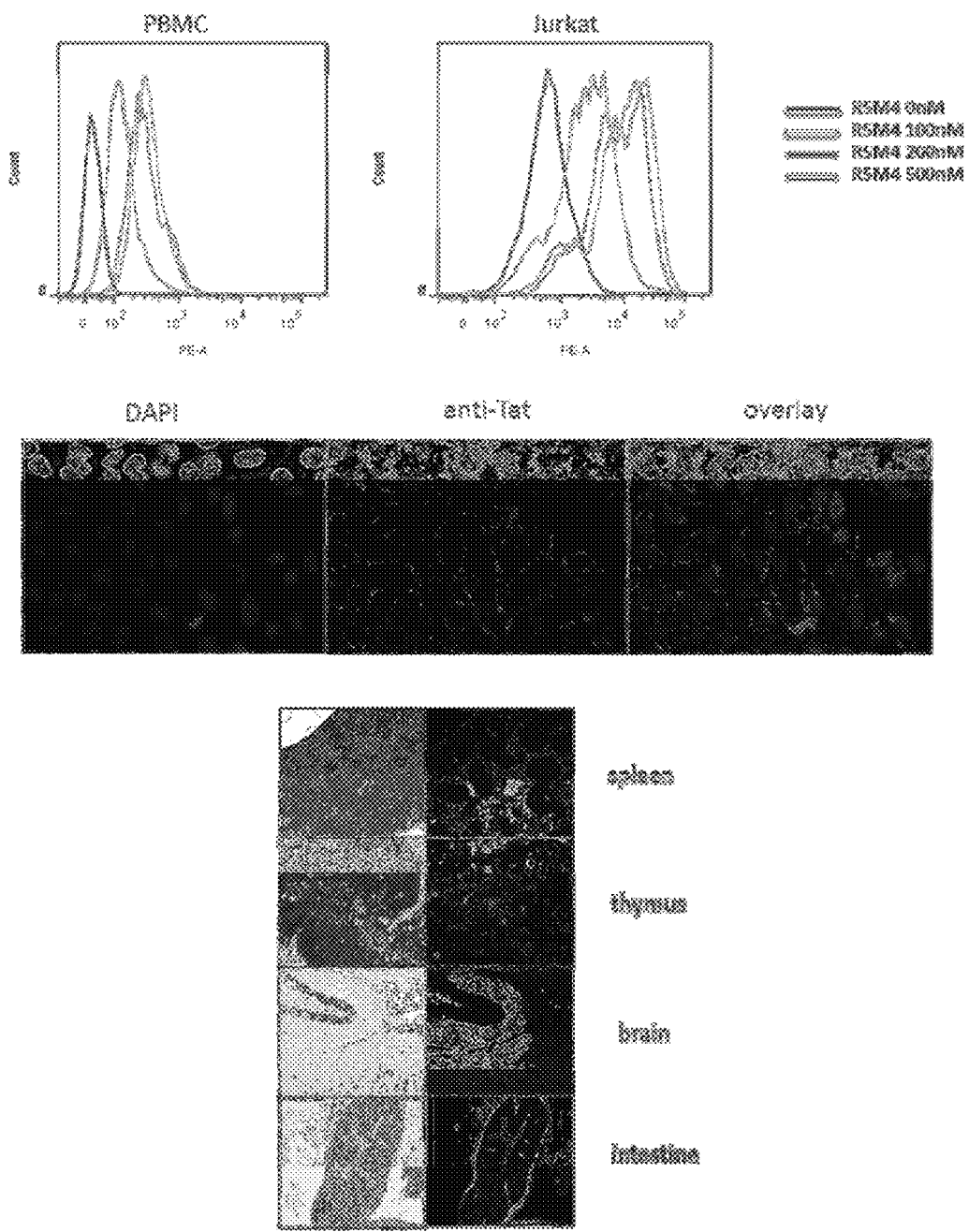
Figure 6:
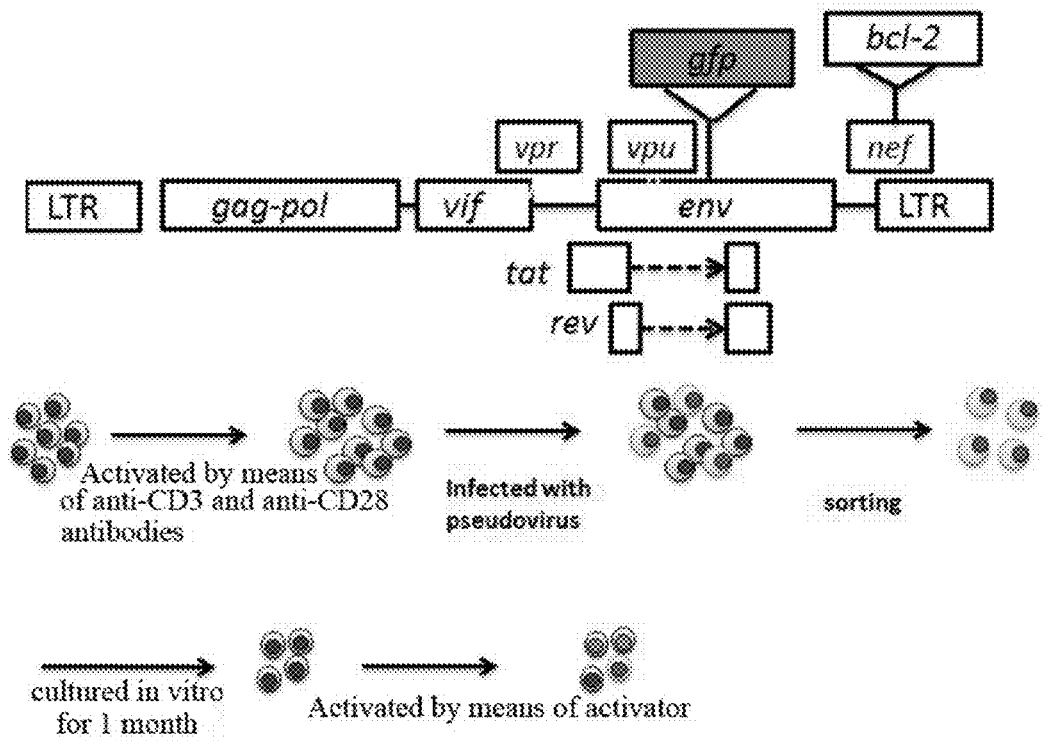
Figure 7:
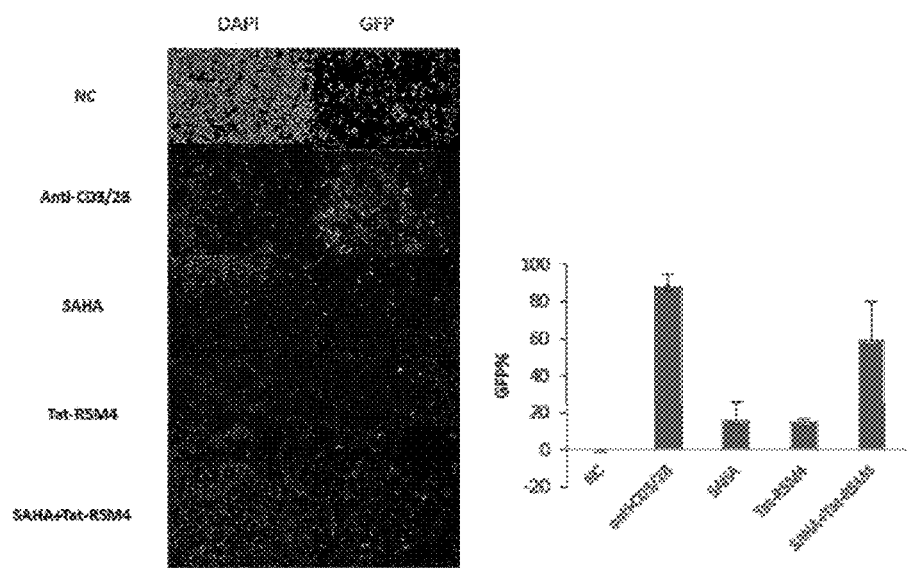
Figure 9:
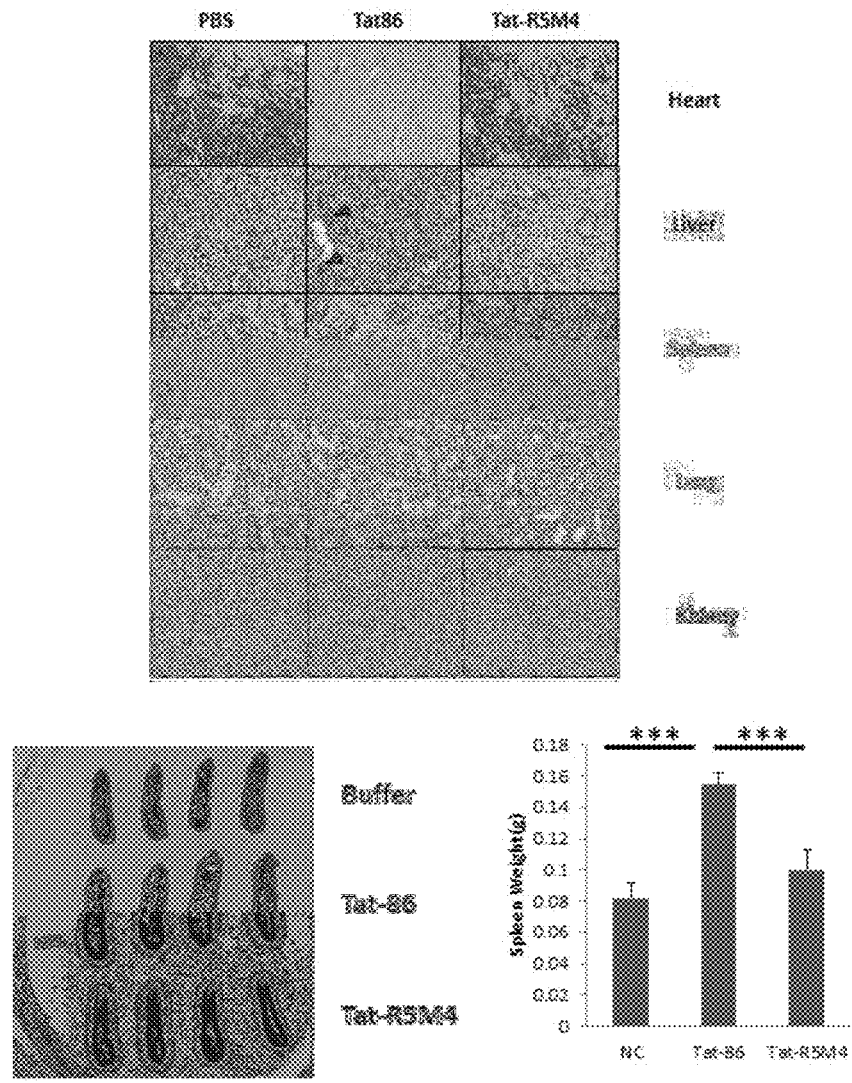

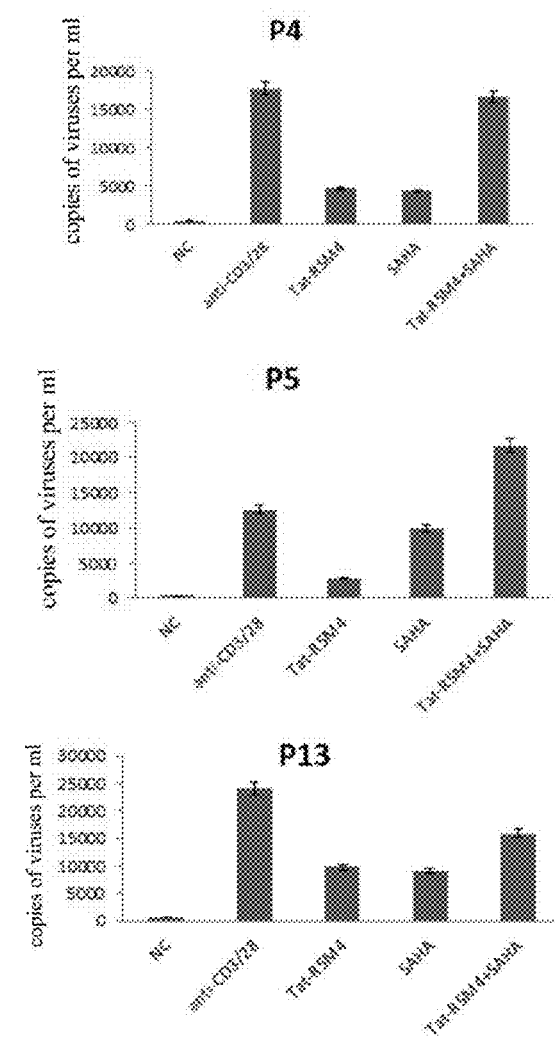
Figure 8
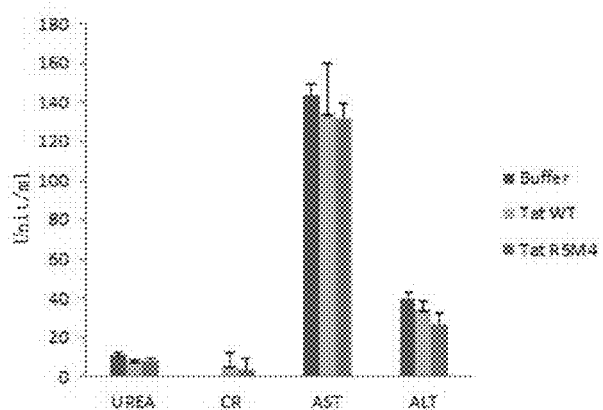

SEQUENCE LISTING

```
<160> NUMBER OF SEQ ID NOS: 4

<210> SEQ ID NO 1
<211> LENGTH: 86
<212> TYPE: PRT
<213> ORGANISM: Artificial Sequence
<220> FEATURE:
<223> OTHER INFORMATION: Tat Protein

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Ala Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Ala Ala Leu Ser Lys Gln Pro Thr Ser Gln Ser Arg Gly Asp
65                  70                  75                  80

Pro Thr Gly Pro Lys Glu
                85

<210> SEQ ID NO 2
<211> LENGTH: 86
<212> TYPE: PRT
<213> ORGANISM: Artificial Sequence
<220> FEATURE:
<223> OTHER INFORMATION: Tat Protein

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ala Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Ala Ala Leu Ser Lys Gln Pro Thr Ser Gln Ser Arg Gly Asp
65                  70                  75                  80

Pro Thr Gly Pro Lys Glu
                85

<210> SEQ ID NO 3
<211> LENGTH: 86
<212> TYPE: PRT
<213> ORGANISM: Artificial Sequence
```

```
<220> FEATURE:
<223> OTHER INFORMATION: Tat Protein

<400> SEQUENCE: 3

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Ala Ala Leu Ser Lys Gln Pro Thr Ser Gln Ala Arg Gly Asp
65                  70                  75                  80

Pro Thr Gly Pro Lys Glu
                85

<210> SEQ ID NO 4
<211> LENGTH: 86
<212> TYPE: PRT
<213> ORGANISM: Artificial Sequence
<220> FEATURE:
<223> OTHER INFORMATION: Tat Protein

<400> SEQUENCE: 4

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Ala Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Ala Ala Leu Ser Lys Gln Pro Thr Ser Gln Ala Arg Gly Asp
65                  70                  75                  80

Pro Thr Gly Pro Lys Glu
                85
```

TRANSACTIVATOR OF TRANSCRIPTION (TAT) PROTEINS AND PREPARATION METHOD

CROSS REFERENCE TO RELATED APPLICATIONS

The present application is a national phase entry under 35 U.S.C. §371 of International Application No. PCT/CN2014/079675, filed Jun. 11, 2014, published as International Publication No. WO 2015/188334 A1, which is hereby incorporated herein by reference.

TECHNICAL FIELD

The present invention relates to an antiviral compound, and more particularly, to an improved Tat protein and preparation method and use thereof.

BACKGROUND

Highly active antiretroviral therapy (HAART) can effectively control the amount of viruses in patients to an undetectable extent, but it is hard to be remove precursor viruses of latently infected HIV-1 (human immunodeficiency virus type 1) after integrated into a genome of a host to form a reservoir pool. Long-term medication is necessary for patients to suppress a viral replication, and a rebound of the viral replication may be caused once withdrawal of drugs. How to clear latent infection of HIV-1 has become a bottleneck problem for completely curing AIDS.

Cytokines such as interleukin-2 (IL-2) and anti-CD3 etc. have been used for activating latent infection of HIV-1, which activate the cells in an overall level, leading to huge poisonous side effects on an organism. A plurality of histone deacetylase inhibitors (HDACi) are also latent activators studied more currently. On one hand, abnormal expressions of other genes are easily caused due to activation of HDACi to genes being broad-spectrum effects; on the other hand, HDACi having better effects in vitro such as valproc acid (VPA) and Vorinostat (ie. Suberoylanilide hydroxamic acid, SAHA), and being not good in clinical manifestations, cannot be put into practical use. Therefore, finding out new, strong in specificity, highly effective and safe latent activators is an urgent mission.

HIV-1 Tat is a specific trans-activation factor of HIV-1, which specifically binds to TAR of HIV-1 5' LTR, raising several hundreds of times the transcription of HIV-1 mRNA. TAT protein is also a critical factor in the latent infection of HIV-1. This protein with cell-penetrating peptides has been proven to have a function of efficiently penetrating cytomembrane; and has been designed as a vaccine for HIV-1 used in clinical experiment, which is relatively safe for human body. However, Tat protein has been proven to have a function of inducing apoptosis, and may affect functions of immunocyte.

SUMMARY OF THE INVENTION

One of the purposes of the present invention is to find out a new anti-HIV approach.

Firstly, provided is a use of a Tat protein in preparing anti-HIV drugs, and TAT-86 is used in the present invention to demonstrate the effect.

More further provided is a use of an attenuated Tat protein in preparing anti-HIV drugs, an amino acid sequence of the attenuated Tat protein is shown as: SEQ NO: 1, SEQ NO: 2, SEQ NO: 3, or SEQ NO: 4.

More further provided is an attenuated Tat protein, an amino acid sequence of which is shown as: SEQ NO: 1 (R4M4), SEQ NO: 2 (R4M5), SEQ NO: 3 (R4M7), or SEQ NO: 4 (R5M4).

Further provided is a method for preparing the above-described attenuated Tat protein, characterized in that, firstly selecting sites for site-directed mutagenesis, performing site-directed mutagensis on these sites in genes of Tat protein, finally obtaining trans-activation functions of a large number of the remaining Tat, and removing apoptotic and other active attenuated proteins therein.

The invention has the following advantages:

1. The purpose of the present invention is to provide several attenuated HIV-1 Tat proteins for activating latent infection of HIV-1.

2. The present invention provides a thought of using a trans-activation protein Tat of HIV-1 itself as a means for activating latent infection, and makes the Tat protein more reliable in safety by modifying the Tat proteins through accumulative mutagenesis.

3. The present invention provides four kinds of attenuated Tat proteins, which can specifically activate latent infection of HIV-1 at a cellular level.

4. The present invention provides a manner for constructing an improved model of latent infection in vitro of HIV-1.

5. The present invention provides a new method for activating latent infection of HIV-1 using a combination of the attenuated Tat protein with SAHA.

6. The attenuated Tat proteins provided by the present invention have no effect on the function of an immunocyte.

7. It is found in the present invention, that the Tat proteins having superior trans-activation activities can effectively raise a transcription of HIV-1 mRNA.

8. The Tat proteins have good membrane-penetrating activities, and can effectively enter cells and various tissues to function.

DESCRIPTION OF FIGURES

FIG. 1: A principle for modifying and screening HIV-1 Tat proteins.

FIG. 2: A diagram of pattern for four kinds of attenuated Tat.

FIG. 3: The four kinds of attenuated Tat can activate a promoter of HIV-1 in Tzm-b1.

FIG. 4: The modification of Tat-R5M4 reduces cytotoxicity and apoptotic activity.

FIG. 5: Tat-R5M4 can effectively penetrate membranes and enter cells and various tissues.

FIG. 6: Construction of a model for latent infection in vitro of HIV-1.

FIG. 7: Tat-R5M4 can effectively activate a model for latent infection in vitro of HIV-1.

FIG. 8: Tat-R5M4 can effectively activate $CD4^+$T cells in latent infection state from peripheral blood of clinical patients.

FIG. 9: Experiment of acute toxicity and detection of immunogenicity.

MODE OF CARRYING OUT THE INVENTION

The present invention has been described in further detail below in combination with the drawings and the specific embodiments. The reagents, equipment and methods used in the present invention are conventional and commercially available reagents and equipment, and conventionally used methods in this technical field, unless otherwise specified.

Embodiment 1: Modification and Detection for Activity of Tat

Over the past decades, the structure and the function of HIV-1 Tat have been studied in great detail. In the present invention, we remove apoptotic activity by accumulating mutagenesis and modification, and retain most of transactivation-active Tat proteins. Since the study for the first three structure domains (amino acids 1-59) of Tat proteins has been very detailed, we initially select amino acids 60-72 studied less to perform point mutagenesis, connect the mutated genes with an eukaryotic expression vector to transfect into Tzm-b1 cells, and examine the activity of luciferase afterwards, wherein only M36, M39, M51, M66, M67, M68, M69, and M77 remain 80% or more of the trans-activation activity. Then, we combine and superpose these mutagenesises, finally obtaining four candidate proteins after six rounds of mutagenesis: R4M4, R4M5, R4M7, and R5M4, wherein R5M4 accumulates at most five point mutagenesises.

Wherein, R4M4 in site-directed mutagenesis has replaced valine at the 36th position with alanine, glutamine at the 66th position with alanine, valine at the 67th position with alanine, and serine at the 68th position with alanine.

Wherein, R4M5 in site-directed mutagenesis has replaced isoleucine at the 39th position with alanine, glutamine at the 66th position with alanine, valine at the 67th position with alanine, and serine at the 68th position with alanine.

Wherein, R4M7 in site-directed mutagenesis has replaced glutamine at the 66th position with alanine, valine at the 67th position with alanine, serine at the 68th position with alanine, and serine at the 77th position with alanine.

Wherein, R5M4 in site-directed mutagenesis has replaced valine at the 36th position with alanine, glutamine at the 66th position with alanine, valine at the 67th position with alanine, serine at the 68th position with alanine, and serine at the 77th position with alanine.

R4M4, R4M5, R4M7 and R5M4 are cloned into a prokaryotic expression vector to perform expression and purification, TZM-b1 cells are treated with the obtained proteins, and the activity of Firefly Luciferase is examined after 48 hours.

This experiment proves that the modified R4M4, R4M5, R4M7, and R5M4 have good transactivation activity in Tzm-b1.

Embodiment 2: Detection for Cytotoxicity and Apoptosis Activity 10 nM, 50 nM, 100 nM, 500 nM, 1 μM, 2 μM, 3 μM and 4 μM of Tat-86 or Tat-R5M4 are co-cultured with TZM-b1 cells, and viabilities of the cells are examined by means of MTS method after 48 hours. 0.1 μg, 0.5 μg, 1 μg, and 2 μg of Tat-86 (subjected to prokaryotic expression according to a conventional technique, cited references: Expression of full length Tat in *E. coli* and its purification) and Tat-R5M4 are co-incubated with Jurkat cells respectively, and double stained by means of Annexin-V-FITC and PE after 48 hours, and apoptosis ratio is examined by flow cytometry.

The present experiment proves that Tat-R5M4 obviously reduces cytotoxicity and an ability inducing apoptosis.

Embodiment 3: Detecting Membrane-Penetrating Activity of Tat-R5M4

To verify whether the membrane-penetrating activity of Tat-R5M4 is affected after mutagenesis, the purified Tat- R5M4 proteins are labeled with NHS-Rhodamine, and a state of Tat entering cells is examined by flow cytometry 6 hours after respectively treating PBMC and Jurkat cells with the labeled proteins. Tat-R5M4 has good membrane-penetrating activity. To detect the distribution situation of Tat-R5M4 in cytoplasms after entering into cells, Tzm-b1 cells are treated with the purified Tat-R5M4 proteins, and then subjected to a detection of immunofluorescence with Tat-R5M4 antibody, and it is found that Tat-R5M4 is distributed mostly in cytoplasm after entering cells, with only a small amount of proteins entering nucleus. To detect the distribution situation of Tat-R5M4 proteins in mice, Tat-R5M4 labeled with NHS-rhodamine is injected into mice through caudal vein, slices prepared from the tissues of spleen, thymus, brain, and intestine etc. are examined after 6 hours, and it is found that Tat-R5M4 is obviously distributed in these tissues.

The present experiment confirms that the modified proteins completely maintain membrane-penetrating characteristics thereof, and can efficiently enter cells and tissues to function.

Embodiment 4: Construction of Latent Infection Model in Vitro of HIV-1

The activated primary $CD4^+T$ cells are infected with pseudoviruses having bcl-2 gene, with a positive rate generally between 5% and 10%. After 3 days of infection, the GFP-positive cells are sorted out by flow sorting, then continue to be cultured in PRM1640 medium added with IL-2, and simultaneously added with CD3 and CD28 antibodies for activating again. After one week, PRM1640 medium without any cell factors is used instead, and after culturing for 3-4 weeks, the cells gradually come into resting state with removal of IL-2. These cells in resting state may be used for detection of latent activator.

Embodiment 5: Activation Role of Tat-R5M4 in $CD4^+T$ Cells from Sources of Latent Infection Model in Vitro of HIV-1 and Clinical Patients The ability of activating latent infection of Tat-R5M4 is examined by means of a system for latent infection constructed in vitro, CD3/CD28 and SAHA are used and treated as positive controls meanwhile, and the proportion of GFP-positive cells is observed by a fluorescence microscope after 3 days.

CD3/CD28 antibodies and SAHA are used as positive controls, and the isolated $CD4^+T$ cells of clinical samples are treated by means of Tat-R5M4 or a combination of Tat-R5M4 with SAHA meanwhile. A supernatant is taken after 18 hours, and then RNA is extracted to examine the content of HIV-1 RNA in the supernatant.

The above experiment proves that Tat-R5M4 can effectively activate $CD4^+T$ cells in latent state from sources of latent infection model in vitro of HIV-1 and clinical patients' samples, and can enhance trans-activation effects thereof in combination with SAHA meanwhile.

Embodiment 6: Acute Toxicity Experiment and Detection of Immunogenicity

To provide subsequent animal experiments with a certain theory support, the toxicity of Tat-R5M4 protein is further examined Firstly, acute toxicity experiments with Babl/c mice indicate that the mice still live well when a dose of tail vein injection reaches 40 mg/ml. Indicators of the mice such as alanine aminotransferase or glutamic-pyruvic transaminase (ALT), aspartate aminotransferase or glutamic oxalacetic transaminase (AST), urea nitrogen (BREA) and CR (creatinine) etc. are examined to be all in normal levels. The pathological sections show that heart, liver, spleen, lungs and kidneys of the mice have all not shown obvious damage, except that a wild type Tat-86 protein causes infiltration of local inflammatory cells in liver, which suggests that Tat-R5M4 is safe with respect to experiments in mice. Meanwhile, obvious intumescence of spleen is found one week later from the tail vein injection of Tat-86, which indicates that Tat-86 may cause obvious immune response, but Tat-R5M4 would not cause a similar phenomenon. Then, the mice are immunized by hypodermic injection with Tat-86 and Tat-R5M4 respectively, and blood is taken upon amputation of tail in 7 days, 14 days, and 21 days respectively, to detect a concentration of Tat antibody, it is found that an amount of the antibody produced by a stimulation of Tat-R5M4 is obviously lower than that of Tat-86.

The present experiment demonstrates that the modified Tat-R5M4 is relatively safe for the mice, has significantly lower immunogenicity, and is more suitable for experiments in vivo than the wild type Tat-86.

What is claimed:

1. A composition comprising an anti-human immunodeficiency virus (HIV) drug, wherein the anti-HIV drug comprises an attenuated transactivator of transcription ("Tat") protein, having an amino acid sequence shown as SEQ NO: 1, SEQ NO: 2, SEQ NO: 3, or SEQ NO: 4.

2. An attenuated transactivator of transcription ("Tat") protein, characterized in that, an amino acid sequence of the attenuated Tat protein is shown as SEQ NO: 1, SEQ NO: 2, SEQ NO: 3, or SEQ NO: 4.

3. A method for preparing the attenuated Tat protein according to claim 2, characterized in that,
   firstly selecting a sites for site-directed mutagenesis in genes of a Tat protein,
   performing site-directed mutagenesis on these Tat protein site,
   removing apoptotic and other active attenuated proteins from the mutated Tat protein, and
   retaining trans-activation functions of the mutated Tat protein to form the attenuated Tat protein.

* * * * *